United States Patent [19]
Ho et al.

[11] Patent Number: 5,451,704
[45] Date of Patent: * Sep. 19, 1995

[54] ALPHA-OLEFIN OLIGOMERIZATION USING SUPPORTED METAL HALIDE CATALYSTS

[75] Inventors: Suzzy C. Ho, Dayton; Margaret M. Wu, Skillman, both of N.J.

[73] Assignee: Mobil Oil Corporation, Fairfax, Va.

[ * ] Notice: The portion of the term of this patent subsequent to Jul. 5, 2011 has been disclaimed.

[21] Appl. No.: 57,029

[22] Filed: May 5, 1993

Related U.S. Application Data

[63] Continuation-in-part of Ser. No. 996,385, Dec. 23, 1992, Pat. No. 5,294,578.

[51] Int. Cl.⁶ ................................. C07C 2/30
[52] U.S. Cl. .................. 585/512; 502/113; 502/152; 502/231; 585/521; 585/523; 585/533
[58] Field of Search ........... 585/512, 533, 532, 521; 502/152, 113, 231

[56] References Cited

U.S. PATENT DOCUMENTS

| | | | |
|---|---|---|---|
| 3,248,343 | 4/1966 | Kelly et al. | 252/442 |
| 3,629,150 | 12/1971 | Addy | 502/231 |
| 4,480,049 | 10/1984 | Johnson | 502/231 |
| 4,665,262 | 5/1987 | Graves | 585/522 |
| 4,670,411 | 6/1987 | Johnson | 502/60 |
| 4,719,190 | 1/1988 | Drago et al. | 502/64 |
| 4,740,652 | 4/1988 | Frame | 585/512 |
| 4,929,800 | 5/1990 | Drago et al. | 585/532 |
| 5,166,410 | 11/1992 | Fried | 554/223 |
| 5,294,578 | 3/1994 | Ho et al. | 502/62 |
| 5,326,920 | 7/1994 | Ho et al. | 585/528 |

OTHER PUBLICATIONS

Inorganic Chemistry, vol. 29, No. 6, 1990, pp. 1186–1192.
Krzywicki et al, "Superacidity of Modified Gamma–$Al_2O_3$", J. C. S. Faraday I., 1980, 76, 1311–1322.

*Primary Examiner*—Asok Pal
*Attorney, Agent, or Firm*—Alexander J. McKillop; Malcolm D. Keen; Laurence P. Hobbes

[57] ABSTRACT

A process for the production of hydrocarbon lubricant basestock comprises contacting $C_2$ to $C_{20}$ alpha-olefin feedstock, or mixtures thereof, e.g., 1-decene, under heterogeneous oligomerization conditions with a catalyst comprising halides of a metal component anchored on an adsorbent inorganic oxide solid, e.g., silica, by an oxygen-metal bond to provide a reaction mixture containing said hydrocarbon lubricant basestock. The catalyst is prepared by contacting the inorganic oxide solid with organic metal halide of the formula RMXY wherein R is alkyl or aryl, M is aluminum, X is halogen and Y is selected from the group consisting of halogen, alkyl, alkenyl, aryl, alkoxy, and amido moieties.

15 Claims, 6 Drawing Sheets

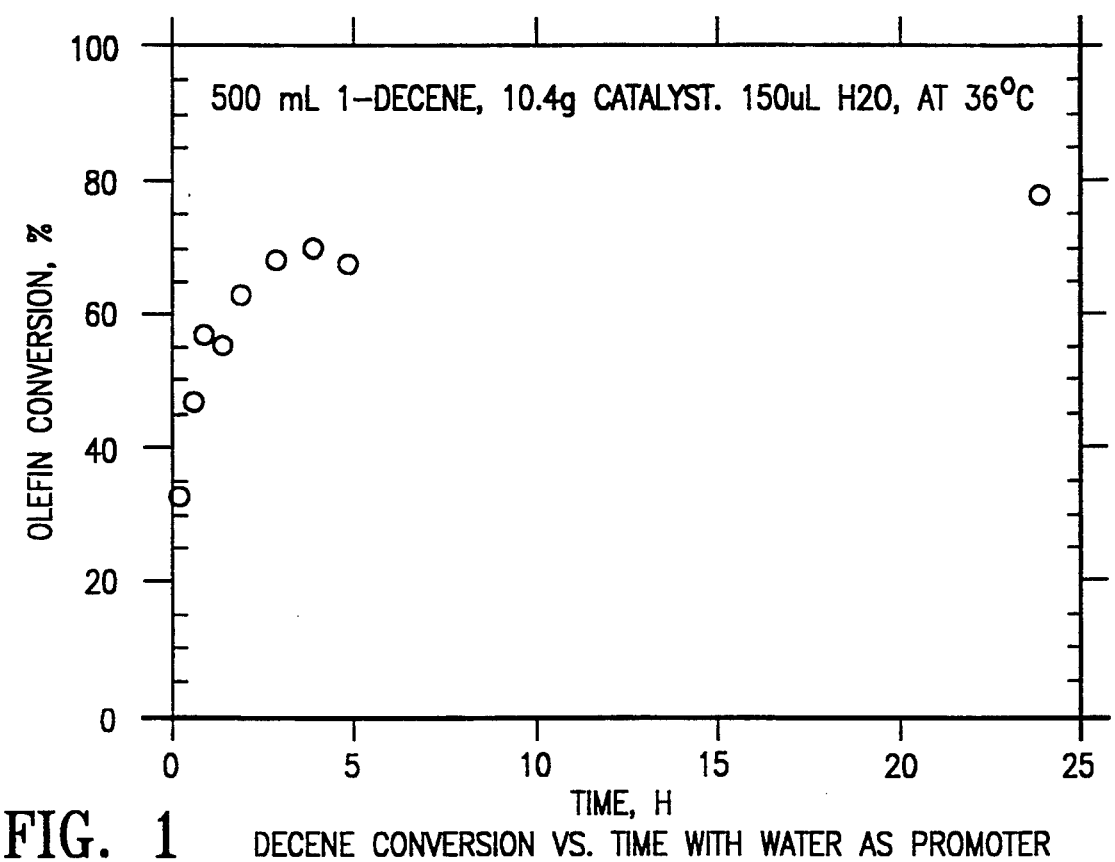
FIG. 1  DECENE CONVERSION VS. TIME WITH WATER AS PROMOTER
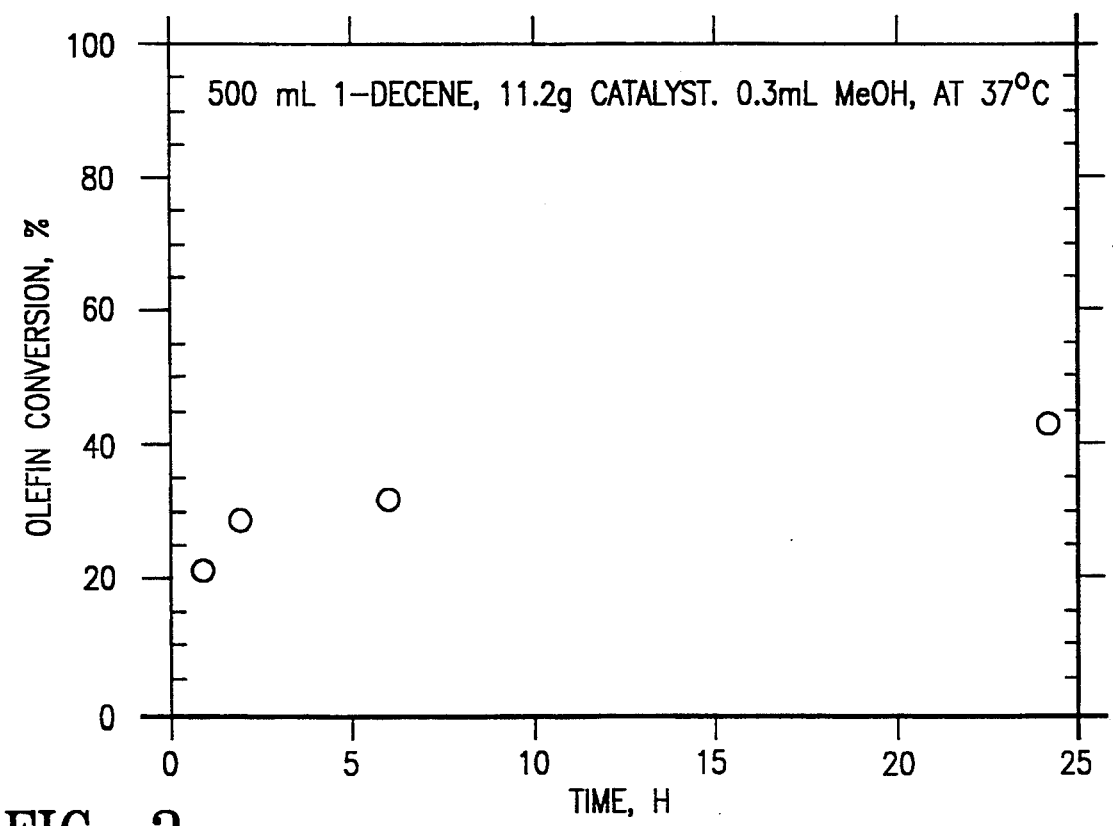
FIG. 2  DECENE CONVERSION VS. TIME WITH METHANOL AS PROMOTER

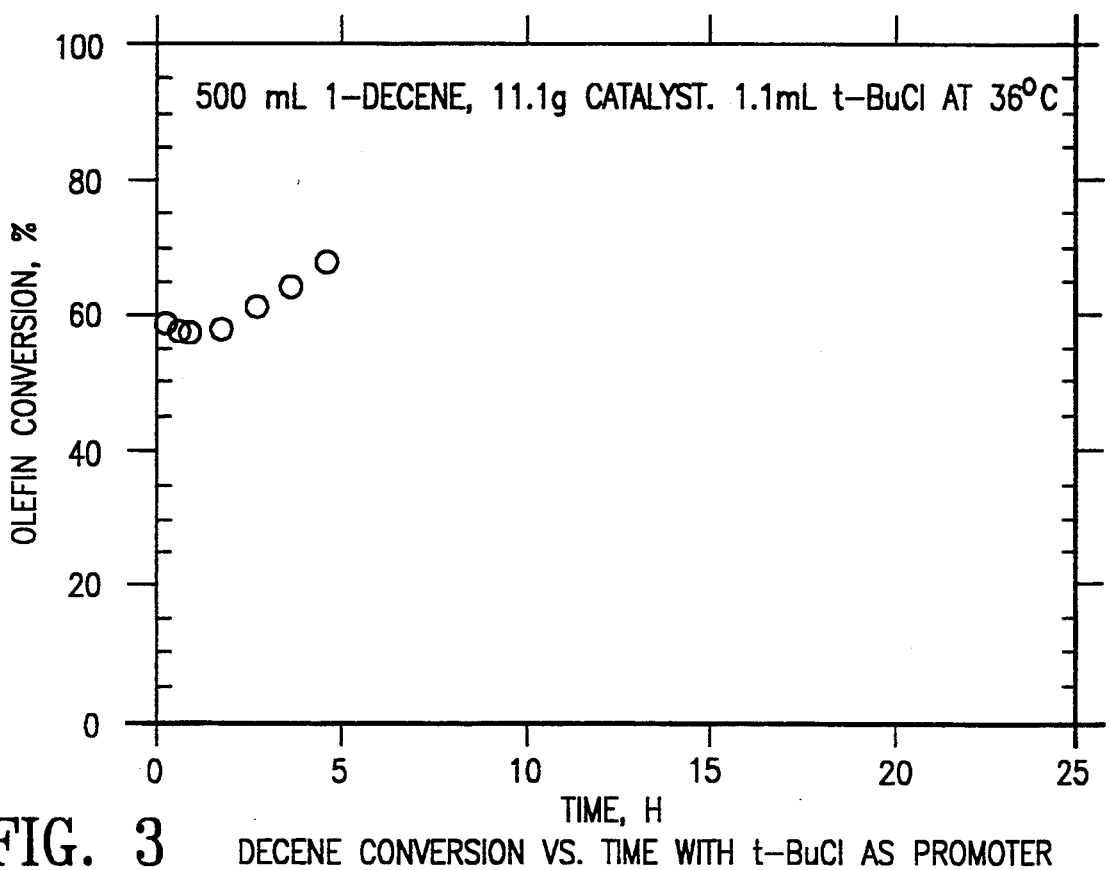
FIG. 3  DECENE CONVERSION VS. TIME WITH t-BuCl AS PROMOTER
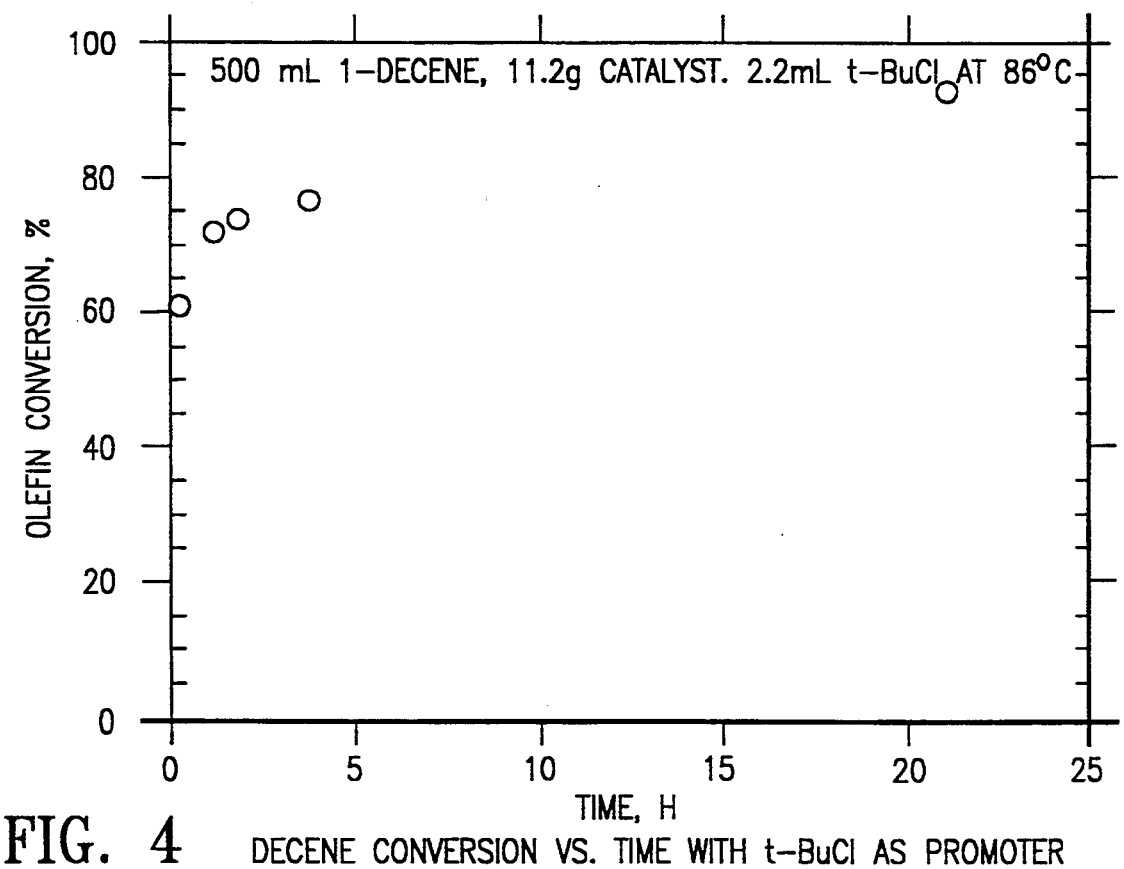
FIG. 4  DECENE CONVERSION VS. TIME WITH t-BuCl AS PROMOTER

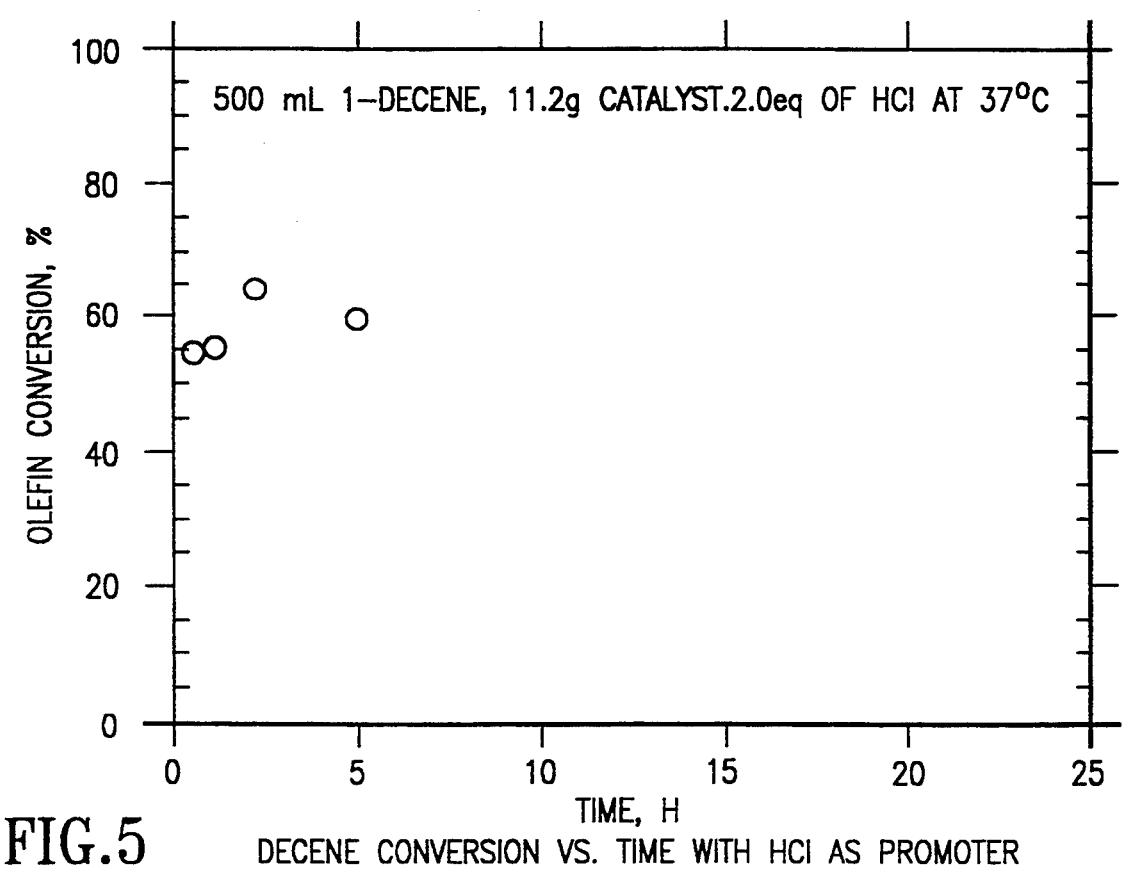
FIG.5 DECENE CONVERSION VS. TIME WITH HCl AS PROMOTER

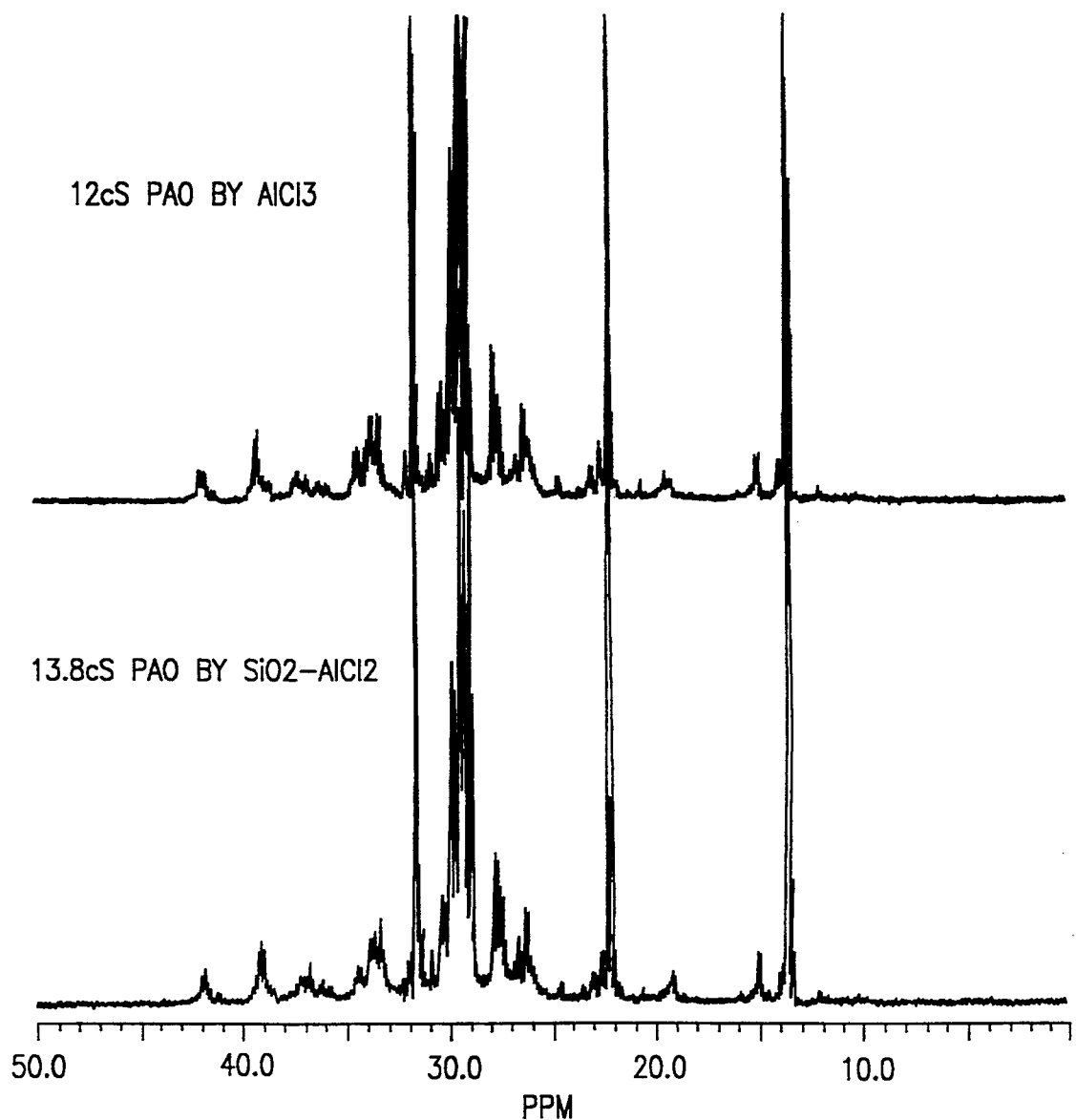
FIG. 6    C-13 NMR COMPARISONS OF PAOs

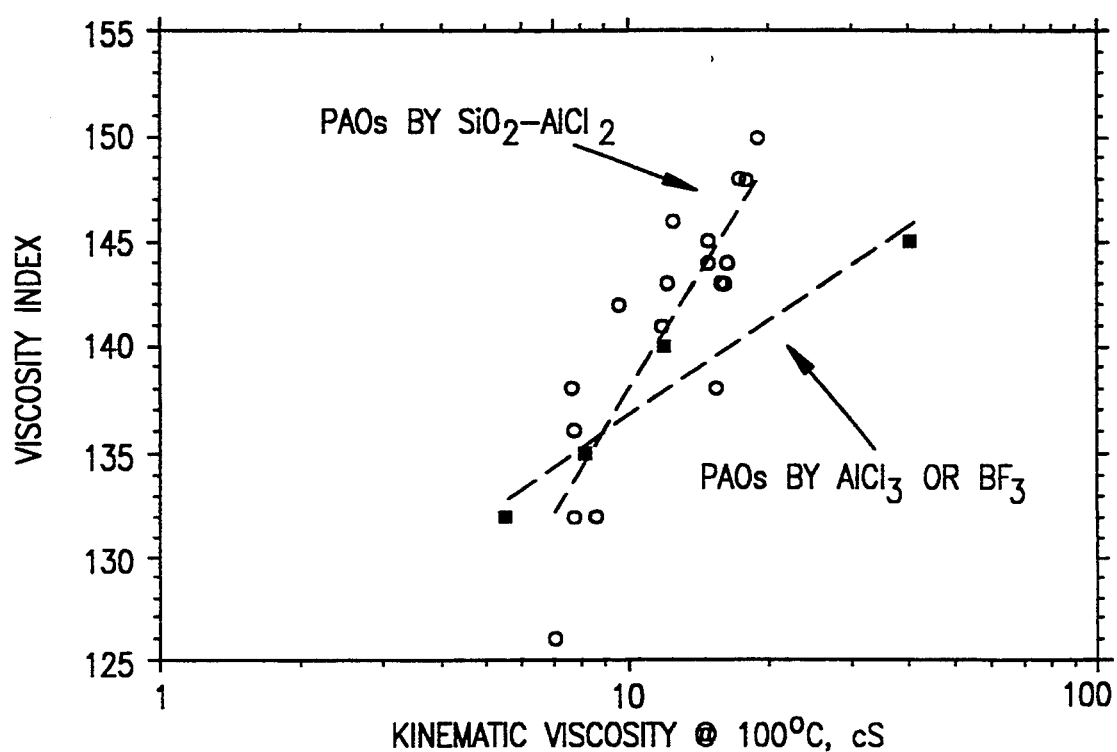
FIG. 7 VISCOMETRIC PROPERTIES OF PAOs BY DIFFERENT CATALYSTS
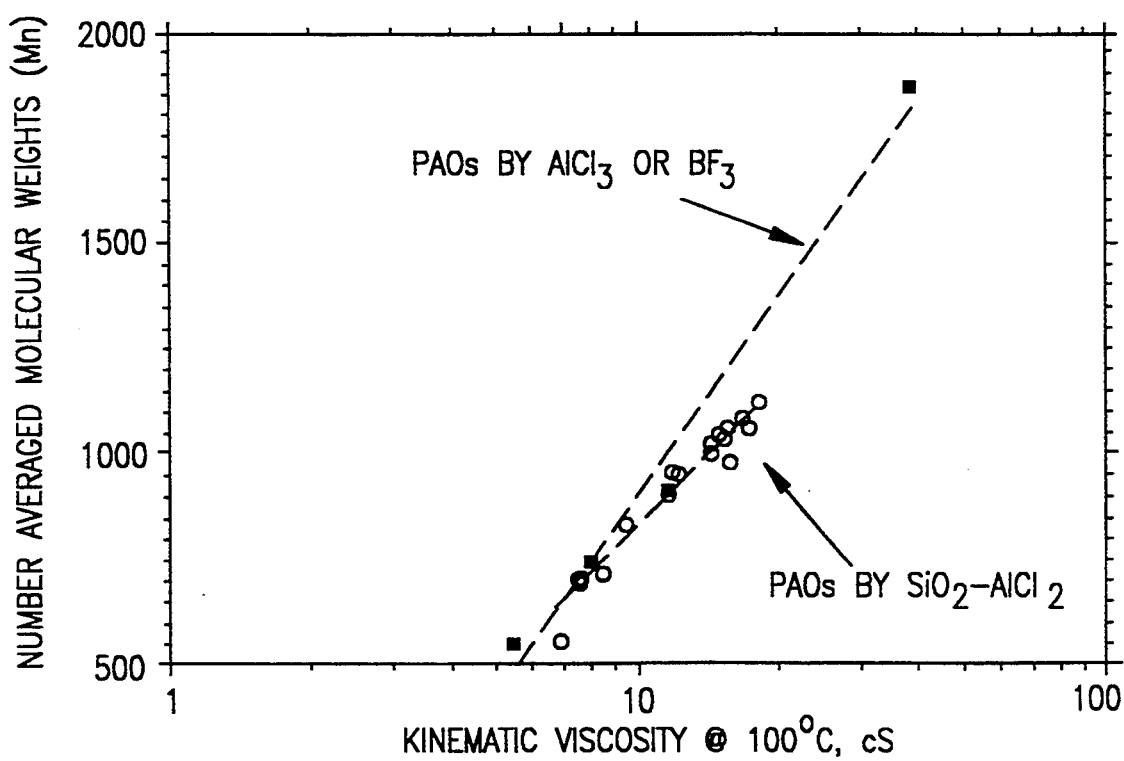
FIG. 8 NUMBER AVERAGED MOLECULAR WEIGHTS OF PAOs

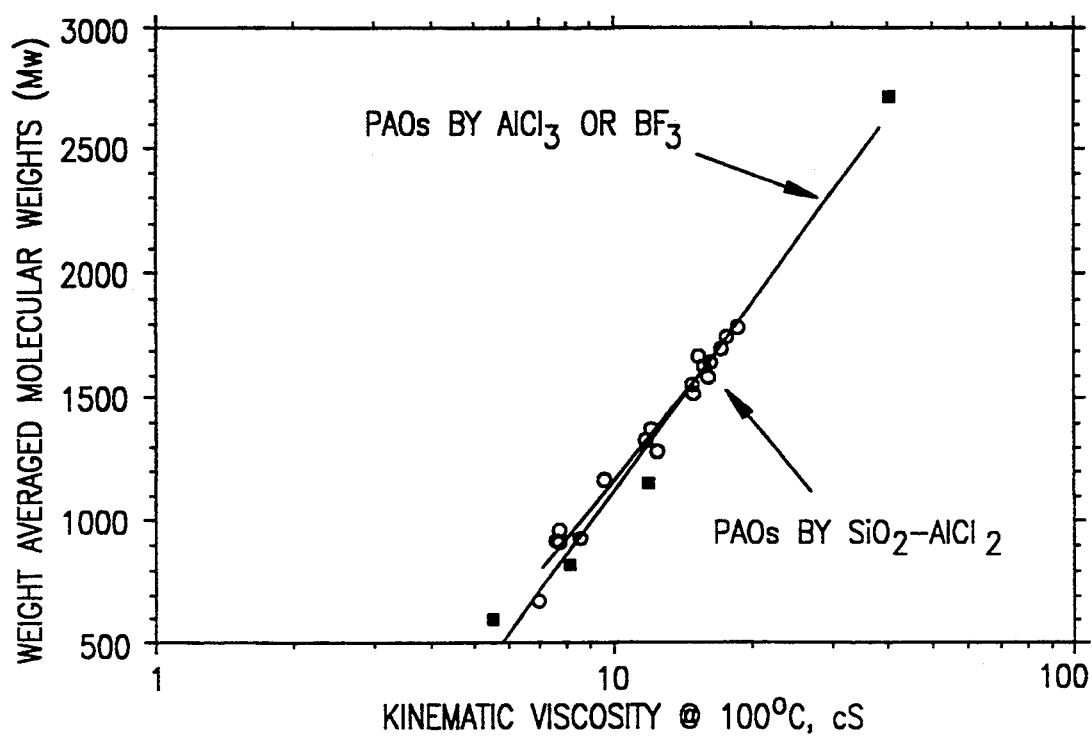
FIG.9  WEIGHT AVERAGED MOLECULAR WEIGHT OF PAOs
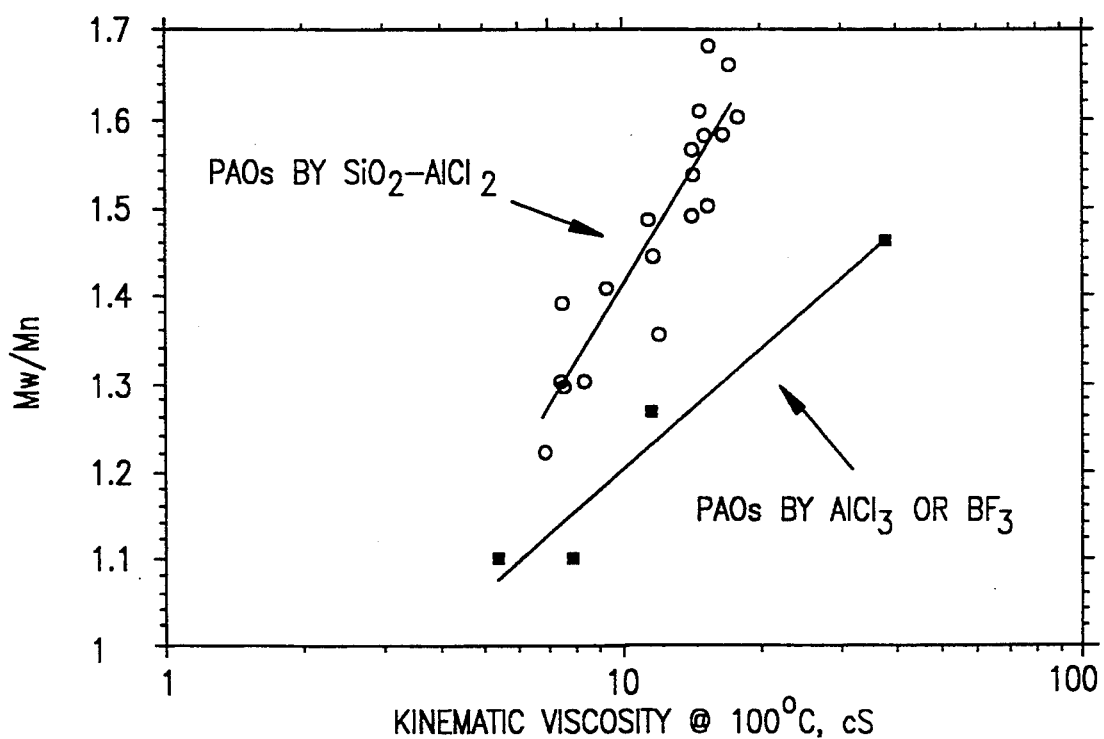
FIG.10  POLYDISPERSITY OF PAOs

ALPHA-OLEFIN OLIGOMERIZATION USING SUPPORTED METAL HALIDE CATALYSTS

REFERENCE TO APPLICATIONS

This application is a continuation-in-part of U.S. patent application Ser. No. 07/996,385, filed Dec. 23, 1992, now U.S. Pat. No. 5,294,578 and is related by subject matter to Ser. No. 08/057,030, filed May 5, 1993, now U.S. Pat. No. 5,326,920.

BACKGROUND OF THE INVENTION

1. Field of the Invention

This invention relates to supported acid catalysts, their method of preparation and use in hydrocarbon conversion reactions, specifically alpha-olefin oligomerization reactions. The catalyst composition contains metal halides on a solid inorganic oxide support. The composition is prepared by reacting an adsorbent solid support containing surface hydroxide groups with organic metal halide wherein said metal is a single element selected from one of Groups IIA, IIB, IIIA, IIIB, IVB, VB, and VIB, e.g., Al, under conditions sufficient for the organic metal halide to react with at least a portion of the surface hydroxyl groups.

2. Prior Art

Conventional Friedel-Crafts catalysts, e.g., $AlCl_3$ and $BF_3$, have been used extensively in many industrial processes as well as in the laboratory. The major drawback of these systems is the need to dispose of large volumes of liquid and gaseous effluents produced during subsequent quenching and product washing. Replacing these processes by those based on heterogeneous catalysis has environmental and economic advantages, e.g., ease of separation, catalyst recycling and elimination of quenching and washing steps.

The literature discloses efforts to anchor $AlCl_3$ onto a solid support. Alumina can be chlorided with $AlCl_3$, HCl, or $Cl_2$. U.S. Pat. No. 3,248,343 to Kelly et al. teaches the treatment of surface hydroxyl-containing supports, e.g., alumina or silica gel, with aluminum halide and thereafter treating with hydrogen halide. Refluxing $AlCl_3$ with solid supports, e.g., silica, in chlorinated solvent, e.g., $CCl_4$, is an alternate way of anchoring Lewis acid onto a support as disclosed in U.S. Pat. No. 4,719,190 to Drago et al and Getty et al , "Preparation, Characterization, and Catalytic Activity of a New Solid Acid Catalyst System," *Inorganic Chemistry*, Vol. 29, No. 6, 1990 1186–1192. However, these methods suffer from incomplete reaction between $AlCl_3$, HCl or $Cl_2$ and the support, resulting in a catalyst that either contains a low concentration of the acidic species or is not very stable due to the leachability of physisorbed or chemisorbed $AlCl_3$ species from the solid support. Krzywicki et al , "Superacidity of Modified Gamma-$Al_2O_3$, "J. C. S. Faraday I, 1980, 76, 1311–1322, teach the treatment of alumina with a metal-alkyl species, e.g., $CH_3AlCl_2$ vapors, to prepare a superacid catalyst which can catalyze the transformation of saturated hydrocarbons. U.S. Pat. No. 4,740,652 to Frame discloses an olefin oligomerization catalyst which comprises a porous support, e.g., silica, and plural metal components, an iron group metal, e.g., Ni, and alkyl aluminum compound, e.g., diethylaluminum chloride and aluminum halide, e.g., aluminum trichloride. Such catalysts are used in transition metal catalyzed chemistry.

BRIEF SUMMARY OF THE INVENTION

The present invention relates to a process for the production of hydrocarbon lubricant basestock which comprises:

contacting $C_2$ to $C_{20}$ alpha-olefin feedstock, or mixtures thereof, under heterogeneous oligomerization conditions with a catalyst composition comprising halides of a metal component anchored on an adsorbent inorganic oxide solid by an oxygen-metal bond to provide a reaction mixture containing said hydrocarbon lubricant basestock;

and separating and recovering said hydrocarbon lubricant basestock.

In a more particular aspect, the present invention relates to a process wherein the metal is a single element selected from one of Groups IIA, IIB, IIIA, IIIB, IVB, VB, and VIB, and the adsorbent inorganic oxide is selected from the group consisting of silica, silica-alumina, clay, crystalline porous silicates, silicoaluminophosphates, titania, vanadia, and rare earth oxides. The contacting can be carried out in the presence of a suitable promoter, for example, one selected from the group consisting of water, methanol, alkyl halide and HCl.

The present invention further relates to a method of alpha-olefin oligomerization which employs a catalyst composition consisting essentially of halides of a single metal component anchored on an adsorbent solid by an oxygen-metal bond.

The catalyst can be prepared by a method which comprises contacting an adsorbent inorganic oxide support containing surface hydroxyl groups with organic metal halide, under conditions sufficient for the organic metal halide to react with at least a portion of the surface hydroxyl groups. The metal can be a single element selected from one of Groups IIA, IIB, IIIA, IIIB, IVB, VB, and VIB, and the adsorbent inorganic oxide support is selected from the group consisting of silica, silica-alumina, clay, crystalline porous silicates, silicoaluminophosphates, titania, vanadia, and rare earth oxides. Reaction between the organic metal halide and the surface hydroxyl group can proceed readily at moderate conditions, e.g., room temperature and atmospheric pressure, eliminating the organic ligand and forming a metal-oxygen bond. For example, aluminum alkyl halide reacts with surface hydroxyl groups of a silanol-containing support as follows:

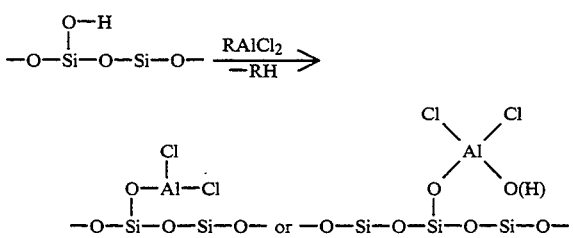

The catalyst compositions thus prepared comprise Lewis acidic catalysts, e.g., $AlCl_3$, $BF_3$, and $GaCl_3$, anchored on the support surface by formation of an oxygen-metal bond. The resulting solid catalysts containing these metals will catalyze hydrocarbon conversion reactions such as olefin oligomerization reactions.

In another aspect, the invention relates to the use in olefin oligomerization of a solid acid catalyst composition which consists essentially of halides of at least one major group element (non-transition elements) on an inorganic oxide adsorbent solid support containing surface silanol groups. Such major group metals include Lewis acidic metals such as Al, B, and Ga. Such a composition is prepared by reacting an adsorbent solid support containing surface silanol groups with organic metal halide wherein said metal is one or more major group elements, e.g., Lewis acidic metals (e.g., Al, B, and Ga), under conditions sufficient for the organic metal halide to react with at least a portion of the surface hydroxyl groups.

DESCRIPTION OF THE FIGURES

FIG. 1 is a graph depicting 1-decene conversion at 36° C. over time using water as a promoter.

FIG. 2 is a graph depicting 1-decene conversion at 37° C. over time using methanol as a promoter.

FIG. 3 is a graph depicting 1-decene conversion at 36° C. over time using t-BuCl as a promoter.

FIG. 4 is a graph depicting 1-decene conversion at 86° C. over time using t-BuCl as a promoter.

FIG. 5 is a graph depicting 1-decene conversion at 37° C. over time using HCl as a promoter.

FIG. 6 is a comparison of the C-13 NMR Spectrum of 14 cS PAO, prepared by the supported $AlCl_2$ catalysts and the C-13 NMR spectrum of a 12 cS PAO prepared by homogeneous $AlCl_3$ catalyst.

FIG. 7 is a comparison of the viscometric properties (VI vs. Kinematic Viscosity at 100° C., cS) of 1-decene oligomers (PAOs) prepared from heterogeneous supported $AlCl_2$ catalysts of the present invention and those prepared from homogeneous $AlCl_3$ or $BF_3$ catalyst.

FIG. 8 is a comparison of the number averaged molecular weights of PAOs ($M_n$) vs. Kinematic Viscosity at 100° C., cS) of 1-decene oligomers (PAOs) prepared from heterogeneous supported $AlCl_2$ catalysts of the present invention and those prepared from homogeneous $AlCl_3$ or $BF_3$ catalyst.

FIG. 9 is a comparison of the weight averaged molecular weights of PAOs ($M_w$) vs. Kinematic Viscosity at 100° C., cS) of 1-decene oligomers (PAOs) prepared from heterogeneous supported $AlCl_2$ catalysts of the present invention and those prepared from homogeneous $AlCl_3$ or $BF_3$ catalyst.

FIG. 10 is a comparison of the polydispersity of PAOs ($M_w/M_n$) vs. Kinematic Viscosity at 100° C., cS) of 1-decene oligomers (PAOs) prepared from heterogeneous supported $AlCl_2$ catalysts of the present invention and those prepared from homogeneous $AlCl_3$ or $BF_3$ catalyst.

DETAILED DESCRIPTION OF THE INVENTION

The inorganic porous support materials useful in the present invention are typically inorganic oxides of silica, silica-alumina, silica-thoria, silica-zirconia, clays, crystalline silicates, e.g., zeolites, and silicoaluminophosphates (SAPOs) and comparable oxides which are porous, and have surface hydroxyl groups, viz., silanol groups. Other suitable inorganic porous support materials include titania, zirconia, alumina, vanadia, and rare-earth oxides which have surface hydroxyl groups.

Preferred silica support materials are amorphous silica, silica gels or xerogels with high porosity, preferably having pores of at least 10 Angstroms, more preferably at least 20 Angstroms, e.g., 20 to 460 Angstroms or 60 to 250 Angstroms. Suitable particle sizes for such silica supports range from 1 to 600 mesh, preferably 30 to 400 mesh, e.g., 30 to 60 or 90 to 300 mesh size. The solid support materials can be calcined, preferably under an inert gas, e.g., nitrogen, at a suitable temperature for a sufficient time to remove physically-bound water and/or to partially remove chemically-bound water. Such temperatures can range from about 100° to 900° C., preferably 300° to 600° C., and contacting times can range from 0.1 to 24 hours, preferably 1 to 8 hours. The extent of loading of the halides of a single metal component on the hydroxyl-containing support can be increased by moderating the calcination carried out upon the support prior to contact with the organic metal halide, e.g, reducing calcination temperatures from about 600° C. to 300° C. This is especially effective with silica gel supports. Generally, after treatment with organic metal halide, the metal halides are present in the amount of 0.01 to 10 mmole/g of the catalyst composition.

Naturally occurring clays which can be used as supports herein include the montmorillonite and kaolin families which include the subbentonites, and the kaolins commonly known as Dixie, McNamee, Georgia and Florida clays, or others in which the main mineral constituent is halloysite, kaolinite, dickite, nacrite or anauxite. Such clays can be used in the raw state as originally mined or initially subjected to calcination, acid treatment or chemical modification.

Zeolitic materials, both natural and synthetic, have been demonstrated in the past to have catalytic properties for various types of hydrocarbon conversion. Certain zeolitic materials are ordered, porous crystalline aluminosilicates having a definite crystalline structure as determined by X-ray diffraction, within which there are a large number of smaller cavities which may be interconnected by a number of still smaller channels or pores. These cavities and pores are uniform in size within a specific zeolitic material. Since the dimensions of these pores are such as to accept for adsorption molecules of certain dimensions while rejecting those of larger dimensions, these materials have come to be known as "molecular sieves" and are utilized in a variety of ways to take advantage of these properties.

Such molecular sieves, both natural and synthetic, include a wide variety of positive ion-containing crystalline aluminosilicates. These aluminosilicates can be described as rigid three-dimensional frameworks of $SiO_4$ and $AlO_4$ in which the tetrahedra are cross-linked by the sharing of oxygen atoms whereby the ratio of the total aluminum and silicon atoms to oxygen atoms is 1:2. The electrovalence of the tetrahedra containing aluminum is balanced by the inclusion in the crystal of a cation, for example an alkali metal or an alkaline earth metal cation. This can be expressed wherein the ratio of aluminum to the number of various cations, such as Ca/2, Sr/2, Na, K or Li, is equal to unity. One type of cation may be exchanged either entirely or partially with another type of cation utilizing ion exchange techniques in a conventional manner. By means of such cation exchange, it has been possible to vary the properties of a given aluminosilicate by suitable selection of the cation. The spaces between the tetrahedra are occupied by molecules of water prior to dehydration.

Prior art techniques have resulted in the formation of a great variety of synthetic zeolites. The zeolites have come to be designated by letter or other convenient symbols, as illustrated by zeolite A (U.S. Pat. No.

2,882,243), zeolite X (U.S. Pat. No. 2,882,244), zeolite Y (U.S. Pat. No. 3,130,007), zeolite ZK-5 (U.S. Pat. No. 3,247,195), zeolite ZK-4 (U.S. Pat. No. 3,314,752), zeolite ZSM-5 (U.S. Pat. No. 3,702,886), zeolite ZSM-11 (U.S. Pat. No. 3,709,979), zeolite ZSM-12 (U.S. Pat. No. 3,832,449), zeolite ZSM-20 (U.S. Pat. No. 3,972,983), zeolite ZSM-35 (U.S. Pat. No. 4,016,245), zeolite ZSM-38 (U.S. Pat. No. 4,046,859), zeolite ZSM-23 (U.S. Pat. No. 4,076,842) and MCM-22 (U.S. Pat. No. 4,954,325) merely to name a few.

Silicoaluminophosphates of various structures are taught in U.S. Pat. No. 4,440,871 include SAPO-5, SAPO-11, SAPO-16, SAPO-17, SAPO-20, SAPO-31, SAPO-34, SAPO-35, SAPO-37, SAPO-40, SAPO-41, SAPO-42, and SAPO-44. Other teachings of silicoaluminophosphates and their synthesis include U.S. Pat. Nos. 4,673,559 (two-phase synthesis method); 4,623,527 (MCM-10); 4,639,358 (MCM-1); 4,647,442 (MCM-2); 4,664,897 (MCM-4); 4,639,357 (MCM-5); 4,632,811 (MCM-3); and 4,880,611 (MCM-9).

Mesoporous siliceous materials are recent developments in catalyst technology having novel pore geometry which are suitable as molecular sieves having openings of at least 8 Angstroms which are used as components of the layered catalyst of the present invention. Such materials can be described as inorganic, porous non-layered crystalline phase material exhibiting, after calcination, an X-ray diffraction pattern with at least one peak at a d-spacing greater than about 18 Angstrom Units and having a benzene adsorption capacity of greater than 15 grams benzene per 100 grams of said calcined material at 50 torr and 25° C. Such materials can further be characterized by substantially uniform hexagonal honeycomb microstructure, with uniform pores having a cell diameter greater than 13 Angstrom units, say, 15 Angstrom Units (preferably in the mesoporous range of about 20–100 A). Most prominent among these ultra-large pore size materials is a class of materials known as M41S which are described further in U.S. Pat. No. 5,102,643, including a metallosilicate called MCM-41, which is usually synthesized with Bronsted acid active sites by incorporating a tetrahedrally coordinated trivalent element, such as Al, Ga, B, or Fe, within the silicate framework. Aluminosilicate materials of this type are thermally and chemically stable, properties favored for acid catalysis; however, the advantages of mesoporous structures may be utilized by employing highly siliceous materials or crystalline metallosilicate having one or more tetrahedral species having varying degrees of acidity. In addition to the preferred aluminosilicates, the gallosilicate, ferrosilicate and borosilicate materials may be employed. Although matrices may be formed with the germanium analog of silicon, these are expensive and generally no better than the metallosilicates.

MCM-41 crystalline structure is readily recognized by its spectrographic characteristics, such as electron micrograph, X-ray diffraction pattern, absorption properties, etc., as described in U.S. Pat. No. 5,098,684.

All of the above patents are incorporated herein by reference.

The organic metal halide employed in the present invention can comprise one or more metal elements selected from Groups IIA, IIB, IIIA, IIIB, IVB, VB, and VIB of the Periodic Table, under conditions sufficient for the organic metal halide to react with at least a portion of the surface hydroxyl groups. Suitable organic metal halides include those represented by the formula RMXY wherein R is alkyl, alkenyl, or aryl, M is an element selected from Groups IIA, IIB, IIIA, IIIB, IVB, VB, and VIB of the Periodic Table, X is halogen and Y is selected from the group consisting of halogen, alkyl, alkenyl, aryl, alkoxy, and amido moities. In one embodiment, R is alkyl, M is a Group IIIA element, e.g., Al, B, or Ga, and Y is selected from the group consisting of halogen, e.g., Cl or Br, and alkyl. A particularly preferred organic metal halide is one wherein RMXY is selected from the group consisting of $EtAlCl_2$, $Me_2AlCl$, $Et_2AlCl$, $Et_2AlCl/EtAlCl_2$, and $Et_2AlOMe$, with $EtAlCl_2$ particularly preferred.

Generally, the support is combined with a suitable solvent in amounts sufficient to form a slurry. The slurry is then combined with the organic metal halide which can also be combined with a suitable solvent in order to facilitate handling and mixing. Such solvents are preferably inert to reaction with the support and organic metal halide. Examples of suitable solvents include alkanes which are liquid under standard conditions such as $C_4$ to $C_{16}$ alkanes, e.g., n-pentane, n-hexane, or n-heptane.

The conditions used to prepare the catalysts of the present invention are those which allow the organic metal halide to react with at least a portion of the surface hydroxyl groups on the adsorbent solid support. Suitable conditions for contacting the support with organic metal halide comprise temperatures of $-78°$ to 120° C., pressures of $10^{31\ 6}$ atm to 10 atm, and reaction time of 0.01 to 10 hours. Preferred conditions include temperatures of 20° to 60° C., pressures of $10^{-1}$ to 1 atm, and reaction time of 0.5 to 2 hours. It is preferred that the catalysts of the present invention be prepared under an inert atmosphere, e.g., nitrogen or helium, in order to prevent unwanted hydrolysis of the organic metal halides. Such conditions can be obtained using conventional Schlenk line techniques.

Following the reaction, the catalyst may be separated from the reaction mixture according to any conventional procedure for removing solids from the liquid solvent medium, e.g., decantation or filtration. The catalyst is ready for use after the drying step as described below. In another method of preparation, the resulting solid can be washed with a suitable liquid, e.g. inert organics, e.g., anhydrous $C_4$ to $C_6$ alkanes, e.g., n-hexane. Such washing is preferably carried out a sufficient number of times to substantially remove excess organic metal halides. The washed catalyst is then dried, preferably under vacuum, at temperatures ranging from 0° to 120° C., preferably 20° to 60° C. The dried catalyst is then stored under inert atmosphere, e.g., in a nitrogen filled box.

The amount of metal halides or organo-metal halides deposited onto the solid can range from 0.01 mmole to 10 mmoles of metal halides or organometal halides per g of catalyst. Generally, the lower calcination temperature for the solid, the more organometal halide one can deposit onto the solid.

The catalyst thus prepared is suited to use in the catalytic conversion of organic, e.g., hydrocarbon feeds. In general, catalytic conversion conditions over the present catalyst include a temperature of from about $-100°$ C. to about 760° C., a pressure of from about 0.1 atmosphere (bar) to about 200 atmospheres (bar), a weight hourly space velocity of from 0.08 to 2000 $hr^{-1}$ and a hydrogen/organic, e.g., hydrocarbon, compound ratio of from 0 to 100.

Non-limiting examples of such conversion processes include: cracking hydrocarbons with reaction conditions including a temperature of 300° to 700° C., a pressure of 0.1 to 30 atmospheres (bar) and a weight hourly space velocity of from 0 1 to 20 hr$^{-1}$; dehydrogenating hydrocarbon compounds with reaction conditions including a temperature of 300° to 700° C., a pressure of 0.1 to 10 atmospheres (bar) and a weight hourly space velocity of from 0.1 to 20 hr$^{-1}$; converting paraffins to aromatics with reaction conditions including a temperature of 100° to 700° C., a pressure of 0.1 to 60 atmospheres (bar) and a weight hourly space velocity of from 0.5 to 400 hr$^{-1}$ and a hydrogen/hydrocarbon ratio of from 0 to 20; converting olefins to aromatics, e.g., benzene, toluene and xylenes, with reaction conditions including a temperature of 100° to 700° C., a pressure of 0.1 to 60 atmospheres (bar) and a weight hourly space velocity of from 0.5 to 400 hr$^{-1}$ and a hydrogen/hydrocarbon ratio of from 0 to 20; converting alcohols, e.g., methanol, or ethers, e.g., dimethylether, or mixtures thereof, to hydrocarbons including aromatics with reaction conditions including a temperature of 275° to 600° C., a pressure of 0.5 to 50 atmospheres (bar) and a weight hourly space velocity of from 0.5 to 100 hr$^{-1}$; isomerizing xylene feedstock components with reaction conditions including a temperature of 230° to 510° C., a pressure of 3 to 35 atmospheres (bar), a weight hourly space velocity of from 0.1 to 200 hr$^{-1}$ and a hydrogen/hydrocarbon ratio of from 0 to 100; disproportionating toluene with reaction conditions including a temperature of 200° to 760° C., a pressure of atmospheric to 60 atmospheres (bar) and a weight hourly space velocity of from 0.08 to 20 hr$^{-1}$.

The catalysts of the present invention are particularly useful in processes which rely on a cationic mechanism, e.g., acidic catalysis reactions. All these reactions can be carried out in a fixed-bed, continuous flow reactor or in a slurry, batch-type operation or continuous stirred tank reactor (CSTR) type operation. Such reactions include olefin oligomerization or polymerization reactions with reaction conditions including a temperature of −100° to 300° C., preferably −50° to 200° C., a pressure of 10$^{-6}$ to 60 atmospheres (bar), preferably 0.1 to 10 atmospheres (bar) and a weight hourly space velocity of from 0.1 to 400, preferably 0.1 to 20; Friedel-Crafts alkylation reactions with olefins, alkyl halides or benzyl halides, with reaction conditions including a temperature of −100° to 300° C., preferably −50° to 200° C., a pressure of 0.1 to 60 atmospheres (bar), preferably 0.1 to 10 atmospheres (bar) and a weight hourly space velocity of from 0.1 to 400, preferably 0.1 to 20; and alkane isomerization reactions with reaction conditions including a temperature of 0° to 400° C., preferably 100° to 300° C., a pressure of 0.1 to 60 atmospheres (bar), preferably 0.1 to 20 atmospheres (bar) and a weight hourly space velocity of from 0.1 to 400, preferably 0.1 to 20.

The catalysts of the present invention are particularly suited to use in oligomerization of alpha-olefins to produce lubricant basestocks. Currently, synthetic lubricant basestock, poly-alpha-olefins (PAO) are manufactured by cationic oligomerization processes using either boron trifluoride or aluminum trichloride as catalysts. With an increase of environmental restrictions on the chemical industries, there is a need to eliminate the waste streams generated by these homogeneous processes by the use of catalyst recycling and the disposal of aqueous waste generated from the quenching and washing steps. An alternative to such additional steps is to use heterogeneous catalyst which has the potential of reducing both aqueous and solid wastes. A solid catalyst can be separated from the liquid products by filtration and thus eliminates the aqueous catalyst quenching and product washing steps which tend to leave residual halides in the products, which can result in greater hydrofinishing catalyst consumption. The use of heterogeneous catalyst is of special utility in preparing lubricant compositions of low halide content, say less than 100 ppm Cl, preferably less than 40 ppm Cl.

The oligomerization conditions comprise temperatures of −70° to 250° C., preferably −20° to 180° C. The yield of $C_{20}+$ oligomer is at least 85 wt % for $C_{30}+$ product having a viscosity of at least 4.0 cS at 100° C. The olefin feedstock is selected from propylene, 1-butene, 1-pentene, 1-hexene, 4-methyl-1-pentene, 1-heptene, 1-octene, 1-decene, 1-dodecene, 1-tetradecene or mixtures thereof, with 1-decene preferred. Also suitable for use are olefins-containing refinery feedstocks or effluents.

The lubricant basestock product of oligomerization can comprise $C_{30}$ to $C_{1300}$ hydrocarbons, has a branch ratio of less than 0.25, preferably less than 0.20, a weight average molecular weight between 280 and 20,000, preferably between 280 and 4,000, a number average molecular weight between 280 and 60,000, preferably between 280 and 2,000, molecular weight distribution between 1.01 and 3.0, preferably between 1.05 and 2.50, a pour point below −20° C., preferably below −40° C., and a viscosity index greater than 80, preferably greater than 120.

In one especially preferred embodiment the oligomerizing of alpha-olefin feedstock can be carried out simultaneously with the contacting of the adsorbent inorganic oxide support with organic metal halide.

For oligomerization of the present invention, the adsorbent component from which the catalyst is prepared can have a pore size of 20 to 400 angstroms, preferably 40 to 400 angstroms, and a particle size of 1 to 400 mesh, preferably 35 to 400 mesh.

In order to more fully illustrate the nature of the invention and the manner of practicing same, the following examples are presented. It will be understood that the examples are illustrative only and that various modifications may be made in the specified parameters without departing from the scope of the invention.

EXAMPLE 1

In a 100 mL Schlenk flask was placed 10 g of 20 A silica gel (calcined at 600° C. under nitrogen for 15 hours and stored under nitrogen atmosphere) and 40 mL of anhydrous hexane. 5 g of 25 wt % solution of EtAlCl$_2$ in hexane was added to the slurry via syringe. During the addition-step a stoichiometric amount of ethane evolution was observed. The mixture was stirred at room temperature for one hour. The supernatant was removed and the solids were washed with 20 mL of anhydrous hexane three times. The solids were dried under vacuum at room temperature or 50° C. for one hour.

EXAMPLES 2–12

The method in Example 1 was used with different silica and reagents as indicated in Table 1.

TABLE 1

Catalyst Preparation

| EXAMPLE | SUPPORT | CALCINATION TEMP* | REAGENT | Al:SUPPORT (mmol:g) |
|---|---|---|---|---|
| 1 | 20A silica | 600° C. | EtAlCl$_2$ | <<1.0:1** |
| 2 | 40A silica | 600° C. | EtAlCl$_2$ | 1.0:1 |
| 3 | 60A silica | 600° C. | EtAlCl$_2$ | 1.0:1 |
| 4 | 150A silica | 600° C. | EtAlCl$_2$ | 1.0:1 |
| 5 | 60A silica | 300° C. | EtAlCl$_2$ | 1.0:1 |
| 6 | 60A silica | 300° C. | EtAlCl$_2$ | 2.0:1 |
| 7 | 60A silica | 600° C. | EtAlCl$_2$ | 2.0:1 |
| 8 | 60A silica | 600° C. | Me$_2$AlCl | 1.0:1 |
| 9 | 60A silica | 600° C. | Et$_2$AlCl | 1.0:1 |
| 10 | 60A silica | 600° C. | Et$_2$AlCl/EtAlCl$_2$ | 1.0:1 |
| 11 | 60A silica | 600° C. | Et$_2$AlOMe | 1.0:1 |
| 12 | 50A MCM-41 | 538° C. | EtAlCl$_2$ | 1.0:1 |
| 13 | gamma Al$_2$O$_3$ | 600° C. | EtAlCl$_2$ | 1.0:1 |

*By titration, SiO$_2$ calcined at 300° C. contains 3.0 mmol of Si—OH/g of SiO$_2$
By titration, SiO$_2$ calcined at 600° C. contains 2.1 mmol of Si—OH/g of SiO$_2$
**Reaction between Si—OH and EtAlCl$_2$ was minimal as indicated by the removal of EtAlCl$_2$ during subsequent hexane wash.

EXAMPLES 14-24

The activities of the catalysts shown in Table 1 were tested for aromatic alkylation with toluene and 1-hexane and the results are shown in Table 2.

a) The activities depend on pore size of the silica. Extremely low hexene conversion was observed for catalyst prepared from the 20 A silica. This is the result of lower amount of Al deposited (see Table 1) on the SiO$_2$ as well as the small pore size. The catalyst prepared from the 40 A silica is less active achieving only 15 % hexene conversion in one hour compared to 99 % conversions of similar catalysts prepared from 60 A and 150 A silica;

b) As expected, the catalyst with two chlorine ligands on the aluminum is more active than those containing at least one alkyl or alkoxy ligand. Since alkyl and alkoxy groups are electron donating, the aluminum center with those ligands are less Lewis acidic than those with two chlorine ligands;

c) Catalysts prepared from supports (Examples 3 and 9) calcined at two different temperatures do not show significant difference in the toluene-hexene alkylation reaction; and d) Catalysts with different aluminum loading cannot be differentiated by the toluene-hexene reaction at room temperature.

TABLE 2

Toluene Alkylation with 1-Hexene
(20 mL of Toluene and 10 mL of 1-Hexene over 0.5 g of Catalyst at Room Temperature)

| EXAMPLE | CATALYST | REACTION TIME, h | % 1-HEXENE CONVERSION | PRODUCT DISTRIBUTION (ALKYLATED) | | |
|---|---|---|---|---|---|---|
| | | | | MONO- | DI- | TRI- |
| 14 | Ex. 1 | 20 | 0.1 | — | — | — |
| 15 | Ex. 2 | 1 | 14.8 | 59.1 | 21.4 | 19.5 |
| 16 | Ex. 3 | 1 | 99.0 | 64.2 | 24.2 | 11.6 |
| 17 | Ex. 4 | 1 | 99.0 | 64.9 | 27.1 | 8.0 |
| 18 | Ex. 5 | 1 | 94.5 | 71.8 | 22.1 | 6.1 |
| 19 | Ex. 6 | 1 | 98.8 | 73.1 | 22.5 | 4.4 |
| 20 | Ex. 7 | 1 | 98.4 | 59.3 | 25.2 | 15.5 |
| 21 | Ex. 8 | 48 | 97.1 | 63.1 | 22.8 | 9.2 |
| 22 | Ex. 9 | 90 | 18.9 | 75.9 | 15.0 | 7.5 |
| 23 | Ex. 10 | 99 | 98.1 | 59.3 | 23.5 | 17.2 |
| 24 | Ex. 11 | 49 | 0.2 | 67.9 | 22.8 | 9.2 |

EXAMPLES 25-34

The catalyst prepared according to Example 3 was used for various Friedel-Crafts aromatic alkylation reactions shown in Table 3.

TABLE 3

Friedel-Crafts Aromatic Alkylation

| Ex. | AROMATIC COMPOUND(1) | ALKYLATING AGENT(2) | REACTANT RATIO (mole) 1:2:CATALYST | CONDITION | CONVERSION ALKYLATING AGENT |
|---|---|---|---|---|---|
| 25 | Benzene | 1-Decene | 222:111:1 | <34° C., 2 h | 99% |
| 26 | Diphenylether | 1-Dodecene | 222:111:1 | 100° C., 3.5 h | 80% |
| 27 | Naphthalene | 1-Dodecene | 222:111:2 | 48° C., 19 h | 98% |
| 28 | Phenol | 1-Dodecene | 111:55:1 | 100° C., 19 h | 1.5% |
| 29 | Benzene | 2-Chlorobutane | 555:28:1 | 50° C., 1 h | 99% |
| 30 | Benzene | Dibromomethane | 555:28:1 | 50° C., 2.5 h | 45% |
| 31 | Benzene | Dichlorotoluene | 555:28:1 | 50° C., 17 h | 21% |
| 32 | Chlorobenzene | Dichlorotoluene | 555:28:1 | 50° C., 1 h | 41% |
| 33 | Benzene | Benzyl chloride | 555:55:1 | 50° C., 2.5 h | 56% |
| 34 | Fluorobenzene | Benzyl chloride | 555:55:1 | 50° C., 19 h | 50% |

Olefin Oligomerization

Catalysts were prepared from dehydrated supports and ethyl aluminum halides following procedures set out in Examples 1 to 13 above. Different pore size (40-258 A) and particle size (35-200 mesh) silica were purchased from the Aldrich Chemical Co. and PQ Corporation. Gamma-alumina was obtained from the Strem Chemical Co. Triethylaluminum, aluminum bromide, aluminum chloride and anhydrous hexanes were obtained from Aldrich. Ethyl aluminum dichloride were purchased from Aldrich and Alfa. Ethyl aluminum dibromide was prepared from triethylaluminum and aluminum tribromide according to the procedures set out in "Comprehensive Organometallic Chemistry", Wilkinson, G. Ed. , Vol. 1, p. 641, Pergammon Press, 1982. In general, all manipulations were carried out under nitrogen in a dry box or using Schlenk line techniques.

Oligomerization reaction was carried out by adding the prepared catalyst to a solution of 1-decene containing water or methanol promoter. Promoter is required in a rigorously dried feed. Otherwise trace amount of water in the feed can act as promoter. The reaction mixture was heated or cooled to maintain the desired temperature for 24 hours. The catalyst was removed by filtration and the filtrate was analyzed for decene conversion by refractive index measurement or by gas chromatography (GC) analysis. The >C$_{30}$ fraction was isolated after the removal of c$_{10}$ and C$_{20}$ products by vacuum distillation, and characterized by gas chromatography, gel permeation chromatography, nuclear magnetic resonance spectroscopy and viscosities.

EXAMPLE 35

The effects of halide ligands on the silica supported catalysts were examined using two different catalysts. The SiO$_2$—AlBr$_2$ catalyst was prepared by treating a 2:1 mixture of AlBr$_3$ and AlEt$_3$ with silica according to the equation below.

$$1 \text{ AlEt}_3 + 2 \text{ AlBr}_3 \longrightarrow 3 \text{ EtAlBr}_2 \xrightarrow[-\text{C}_2\text{H}_6]{\text{SiO}_2} \text{SiO}_2\text{—AlBr}_2$$

The activities of the SiO$_2$—AlBr$_2$ catalysts are considerably less than the corresponding SiO$_2$—AlCl$_2$ for 1-decene oligomerizations (51% vs. 70% olefin conversions).

TABLE 4

| Al Species | Conversion | C$_{20}$ | Lube | Visc | VI |
|---|---|---|---|---|---|
| AlBr$_2$ | 51% | 82.4% | 91.3% | 18.7 cS | 150 |
| AlCl$_2$ | 70% | 22.1% | 77.9% | 16.2 cS | 144 |

Catalyst: 35–60 mesh, 60A SiO$_2$ calcined at 600° C., 1.5 mmol Al/g
Conditions: 0.5 eq H$_2$O, Olefin:Catalyst = 30:1, 24° C., 24 h

EXAMPLE 36

The effects of support type were examined using two different catalysts prepared from gamma-alumina and silica, two readily available supports that have similar surface areas and pore sizes. Under the same conditions, decene conversions over the alumina supported AlCl$_2$ catalyst were significantly lower than the silica supported catalyst (13% vs. 59%). The difference in catalyst activities may be attributed to the electronic properties of the supports as AlCl$_2$ on a "basic" alumina is less Lewis acidic than the AlCl$_2$ supported on a "neutral" silica. Although the activities of the Al$_2$O$_3$—AlCl$_2$ catalyst are low for 1-decene oligomerizations, it is active for Friedel-Crafts aromatic alkylation as well as isobutane-butene alkylation reactions as shown in Table 5 below.

TABLE 5

| Support | Conversion | C$_{20}$ | Lube | Visc | VI |
|---|---|---|---|---|---|
| Al$_2$O$_3$ | 13% | — | — | — | — |
| 60A SiO$_2$ | 59% | 21.2% | 78.8% | 17.9 cS | 148 |

Catalyst: 35–60 mesh, calcined at 600° C., 0.9 mmol AlCl$_2$/g
Conditions: 0.5 eq H$_2$O, Olefin:Catalyst = 30:1, 24° C., 24 h

EXAMPLE 37

The effects of silica particle sizes were examined using three different catalysts prepared from different particle sizes of silica, (35–60, 100–200, and 200–425 mesh). Catalysts made from smaller particle size silica (>100 mesh) silica show slightly higher olefin conversions than catalysts prepared from the larger particle size silica (35–60 mesh). No great differences were found between catalysts based on 100–200 mesh and 200–425 mesh silica. The three catalysts based on different particle size silica yielded products of similar viscosities as shown in Table 6 below.

TABLE 6

| SiO$_2$ Support | Conversion | C$_{20}$ | Lube | Visc | VI |
|---|---|---|---|---|---|
| 35–60 mesh | 71% | 20.2% | 79.8% | 15.8 cS | 143 |
| 100–200 mesh | 83% | 20.8% | 79.2% | 14.9 cS | 144 |

Catalyst: 150A SiO$_2$, calcined at 600° C., 0.9 mmol AlCl$_2$/g
Conditions: 0.5 eq H$_2$O, Olefin:Catalyst = 30:1, 24° C., 24 h

EXAMPLE 38

The effects of silica pore sizes were examined using four different catalysts prepared from different pore sizes of silica, 40 A, 60 A, 150 A and 258 A. Under the same conditions decene conversions increased with silica pore size up to 150 A. Above that, the advantage of a large pore silica (e.g. 258 A) was not obvious. The product viscosities decreased from 18 cS to 12 cS as silica pore sizes increase from 60 A to 258 A as shown in Table 7 below.

TABLE 7

| SiO$_2$ Pore Size | Conversion | C$_{20}$ | Lube | Visc | VI |
|---|---|---|---|---|---|
| 40A | 7% | — | — | — | — |
| 60A | 60% | 21.2% | 78.7% | 17.9 cs | 148 |
| 150A | 71% | 20.2% | 79.8% | 15.8 cS | 143 |

Catalyst: 35–60 mesh SiO$_2$, calcined at 600° C., 0.9 mmol AlCl$_2$/g
Conditions: 0.5 eq H$_2$O, Olefin:Catalyst = 30:1, 24° C., 24 h

| | | | | | |
|---|---|---|---|---|---|
| 150A | 83% | 20.8% | 79.2% | 14.9 cS | 144 |
| 258A | 72% | 25.2% | 74.8% | 11.9 cS | 141 |

Catalyst: 100–200 mesh SiO$_2$, calcined at 600° C., 0.9 mmol AlCl$_2$/g
Conditions: 0.5 eq H$_2$O, Olefin:Catalyst = 30:1, 24° C., 24 h

EXAMPLE 39

Calcination temperatures for the silica support were examined using catalysts prepared from silica dehydrated at 300° C. and 600° C. The former yielded significantly more dimers. Silica dehydrated at 600° C. is believed to contain only isolated silanols resulting in Al anchoring only through the formation of one Al—O—Si bond. Silica dehydrated at 300° C. is thought to contain adjacent as well as isolated silanol groups on the surface resulting in two kinds of alumina bound to the surface. Alumina containing two O—Si ligands are much less Lewis acidic than Al with one O—Si ligand. The large amounts of decene dimers made by the 300° C. dehydrated silica may be formed by the less acidic aluminum centers which can not catalyze further oligomerization of the dimers to form higher oligomers due to its inherent lower activities. Results are given below in Table 8.

TABLE 8

| Calc. Temp. | Conversion | C$_{20}$ | Lube | Visc | VI |
|---|---|---|---|---|---|
| 300° C. | 66% | 61.5% | 38.5% | 7.0 cS | 126 |
| 600° C. | 59% | 47.4% | 52.7% | 7.7 cS | 136 |

Catalyst: 35–60 mesh, 60A, calcined at 600° C.
Conditions: 0.5 eq H$_2$O, Olefin:Catalyst = 30:1, 24° C., 24 h

EXAMPLE 40

The effects of varying amounts of AlCl$_2$ on the silica surface of the catalysts were examined. A significant increase of Al on the support (by 67%) improves olefin conversion only slightly, from 60% to 68% as shown in Table 9 below.

TABLE 9

| AlCl$_2$/g | Conversion | C$_{20}$ | Lube | Visc | VI |
|---|---|---|---|---|---|
| 0.9 mmol | 60% | 21.2% | 78.7% | 17.9 cS | 148 |
| 1.5 mmol | 68% | 22.1% | 77.9% | 16.2 cS | 144 |

EXAMPLE 41

The effect of varying promoters for 1-decene oligomerization with the catalysts was examined. No significant differences in olefin conversions and product viscosities were observed between the two promoters as shown in Table 10 below.

TABLE 10

| Promoter | Conversion | C$_{20}$ | Lube | Visc | VI |

TABLE 10-continued

| | | | | | |
|---|---|---|---|---|---|
| 1.0 eq MeOH | 54% | 24.0% | 76.0% | 15.9 cS | 146 |
| 1.0 el H$_2$O | 64% | 22.8% | 77.2% | 16.8 cS | 146 |

Catalyst: 35–60 mesh, 60A SiO$_2$, calcined at 600° C., 0.9 mmol/g AlCl$_2$/g
Conditions: Olefin:Catalyst = 30:1, 24° C., 24 h

| | | | | | |
|---|---|---|---|---|---|
| 0.5 eq MeOH | 80% | 19.6% | 80.4% | 13.8 cS | 142 |
| 0.5 eq H$_2$O | 80% | 32.4% | 67.6% | 13.8 cS | 139 |

Catalyst: 35–60 mesh, 60A SiO$_2$, calcined at 600° C., 0.9 mmol/g AlCl$_2$/g
Conditions: Olefin:Catalyst = 30:1, 50° C., 24 h

EXAMPLE 42

The effect of varying amounts of promoter for 1-decene oligomerization with the catalysts was examined. The final olefin conversion, product distribution and product properties were similar between reactions with varying amounts of promoters as shown in Table 11 below.

TABLE 11

| Promoter | Conversion | C$_{20}$ | Lube | Visc | VI |
|---|---|---|---|---|---|
| 1.0 eq MeOH | 54% | 24.0% | 76.0% | 15.9 cS | 146 |
| 1.0 eq H$_2$O | 64% | 22.8% | 77.2% | 16.8 cS | 146 |

Catalyst: 35–60 mesh, 60A SiO$_2$ calcined at 600° C., 0.9 mmol/g AlCl$_2$/g
Conditions: Olefin:Catalyst = 30:1, 24° C., 24 h

| | | | | | |
|---|---|---|---|---|---|
| 0.5 eq MeOH | 80% | 19.6% | 80.4% | 13.8 cS | 142 |
| 0.5 eq H$_2$O | 80% | 32.4% | 67.6% | 13.8 cS | 139 |

Catalyst: 35–60 mesh, 60A SiO$_2$, calcined at 600° C., 0.9 mmol/g AlCl$_2$/g
Conditions: Olefin:Catalyst = 30:1, 50° C., 24 h

EXAMPLE 43

Since water and methanol (as any oxygenates and moisture present in the olefin feed) can react with surface AlCl$_2$ to eliminate HCl and form Al—OR and thus permanently deactivate the catalyst, alternative promoters, such as t-BuCl or HCl which will not deactivate the aluminum center were examined.

FIGS. 1 to 5 depict decene conversion over time with water, (FIG. 1), methanol (FIG. 2), t-BuCl (FIGS. 3 and 4) at 36° C. and 86° C., respectively, and HCl (FIG. 5). Both t-butyl chloride and HCl gave higher olefin conversion at shorter reaction time than either water or methanol as can be seen in FIGS. 1 to 5.

However, even with alkyl halide or HCl promoter, the rate of olefin conversion decreased rapidly over time, possibly resulting from oligomeric product remaining inside the silica pores thereby limiting the diffusion of 1-decene to the active center. To minimize this, experiments were carried out wherein catalyst and t-butyl chloride were added in portions to 1-decene so reaction temperature was maintained at 37° C. The reaction was kept at 37° C. for a few hours and then heated to 84° C. Olefin conversion was monitored and the results summarized in Tables 12 to 15 below. In all four cases it was found that after reaching a certain level of conversion, no significant improvement was achieved by prolonging reaction time. Higher olefin conversion was observed after raising reaction temperature to increase the diffusion rates of both reactant and product (compare Tables 12 and 13).

TABLE 12

| Temperature | Time (cum) | Conversion, % |
|---|---|---|
| 36° C. | 3 h | 45 |
| 36° C. | 21 h | 64 |
| 85° C. | 6 h | 79 |
| 85° C. | 20 h | 94 |

500 ml 1-decene, 11.7 g catalyst, 1.05 ml t-BuCl

TABLE 13

| Temperature | Time (cum) | Conversion, % |
|---|---|---|
| 37° C. | 5.5 h | 57 |
| 85° C. | 1 h | 80 |
| 85° C. | 18 h | 94 |

500 ml 1-decene, 11.2 g catalyst, 1.1 ml t-BuCl

TABLE 14

| Temperature | Time (cum) | Conversion, % |
|---|---|---|
| 38° C. | 6 h | 56 |
| 85° C. | 16 h | 94 |

500 ml 1-decene, 13.7 g catalyst, 1.2 ml t-BuCl

TABLE 15

| Temperature | Time (cum) | Conversion, % |
|---|---|---|
| 38° C. | 3 h | 45 |
| 84° C. | 3 h | 75 |
| 84° C. | 19 h | 86 |

500 ml 1-decene, 8.9 g catalyst, 0.68 ml t-BuCl

EXAMPLE 44

The effect of increased reaction temperatures for 1-decene oligomerization with the catalysts was examined. In general, higher reaction temperatures afforded lower viscosity products and more dimer yields as shown in Table 16 below. The absolute temperature and viscosity relationships depend on individual catalysts which can vary in support particle size, pore size, dehydration temperatures and aluminum loadings.

TABLE 16

| Rxn Temp. | Conversion | C$_{20}$ | Lube | Visc | VI |
|---|---|---|---|---|---|
| 24° C. | 78% | 19.5% | 80.5% | 14.8 cS | 144 |
| 50° C. | 79% | 26.5% | 73.5% | 9.6 cS | 142 |
| 70° C. | 72% | 30.6% | 69.4% | 7.6 cS | 138 |
| 100° C. | 80% | 35.3% | 64.7% | 7.7 cS | 132 |

Catalyst: 100–200 mesh, 150A SiO$_2$, calcined at 600° C., 0.9 mmol AlCl$_2$/g
Conditions: Olefin:Catalyst = 30:1, 24 h

| | | | | | |
|---|---|---|---|---|---|
| 50° C. | 78% | 31.4% | 68.6% | 12.5 cS | 146 |
| 100° C. | 76% | 46.0% | 54.0% | 8.6 cS | 132 |

Catalyst: 35–60 mesh, 60A SiO$_2$, calcined at 600° C., 1.35 mmol AlCl$_2$/g
Conditions: Olefin:Catalyst = 30:1, 24 h

EXAMPLE 45

Oligomerization of 1-decene using a prepared catalyst was carried out by adding the catalysts to a solution of 1-decene containing promoter. In-situ catalysts were generated by adding EtAlCl$_2$ to a slurry of dehydrated silica in 1-decene followed by addition of the promoter according to the following equation:

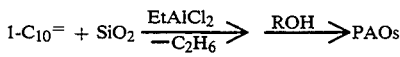

$$1\text{-}C_{10}^= + SiO_2 \xrightarrow[-C_2H_6]{EtAlCl_2} \xrightarrow{ROH} PAOs$$

Both catalyst showed similar activities toward oligomerization of 1-decene. The in-situ generated catalysts yielded products of slightly higher viscosities than products from the prepared catalysts as shown in Table 17 below.

TABLE 17

| 1-Decene | Catalyst | Conversion | C$_{20}$ | Lube | Visc | VI |
|---|---|---|---|---|---|---|
| 90 g | 3 g .9 mmol AlCl$_2$/g | 78% | 19.5% | 80.5% | 14.8 cS | 144 |
| 90 g | *2.7 g SiO$_2$ | 80% | 18.5% | 81.5% | 17.3 cS | 148 |

TABLE 17-continued

| 1-Decene | Catalyst | Conversion | C20 | Lube | Visc | VI |
|---|---|---|---|---|---|---|
| | 2.7 mmol EtAlCl2 | | | | | |

SiO2: 100–200 mesh, 150A, calcined at 600° C.
*In-situ generated

EXAMPLE 46

The effect of increased amounts of catalyst were studied. Olefin conversions increased but product viscosities decreased with increasing amounts of catalysts used in the reactions. At low catalyst loadings the high concentrations of 1-decene near the catalytic centers favor the oligomer growth process to form higher molecular weight products and thus increase viscosity as shown in Table 18 below.

TABLE 18

| *Catalyst Chg | Conversion wt % | Lube Sel. (C30+) | Visc | VI |
|---|---|---|---|---|
| 1.0% | 54 | 63.5% | 16.0 cS | 143 |
| 2.5% | 73 | 67.1% | 14.8 cS | 145 |
| 5.0% | 89 | 84.4% | 12.2 cS | 143 |

SiO2: 100–200 mesh, 150A, calcined at 600° C., 0.9 mmol AlCl2/g.
*In-situ generated

EXAMPLE 47

A catalyst was prepared from EtAlCl2 generated from the disproportionation of AlEt3 and AlCl3 in the stoichiometry shown below:

$$1 \text{ AlEt}_3 + 2 \text{ AlBr}_3 \longrightarrow 3 \text{ EtAlBr}_2 \xrightarrow[-C_2H_6]{SiO_2} SiO_2-AlCl_2$$

No significant differences between catalysts made from the commercial EtAlCl2 available from Aldrich and the less expensive product prepared by disproportionation of AlEt3 and AlCl3 were found in 1-decene oligomerization reactions as shown below in Table 19.

TABLE 19

| Al Source | Conversion wt % | Lube Sel. (C30+) | Visc | VI |
|---|---|---|---|---|
| EtAlCl2 | 78 | 80.5 | 14.8 cS | 144 |
| AlEt3/AlCl3 | 75 | 85.8 | 14.2 cS | 143 |

SiO2: 100–200 mesh, 150A, calcined at 600° C., 0.9 mmol AlCl2/g.
Conditions: 1.0 eq H2O, 24° C., 24 h

EXAMPLE 48

Poly alpha-olefin products prepared by the silica supported AlCl2 catalysts were compared to PAOs produced by homogeneous BF3 and AlCl3 processes. C-13 NMR Spectrum of 14 cS PAO, prepared by the supported AlCl2 catalysts, resembles the spectrum of a 12 cS PAO prepared by homogeneous AlCl3 catalyst as shown in FIG. 6. The spectra of both PAOs show the presence of short chain branches, methyl, ethyl and propyl groups, at the backbones.

The viscosity and VI relationships of the PAOs prepared by the silica supported AlCl2 catalysts and those produced by homogeneous BF3 and AlCl3 processes are shown in FIG. 7. In the 10–20 cS range, the PAOs made from the heterogeneous catalysts have slightly higher VIs which can be attributable to the differences in reaction temperatures of the two processes. In the homogenous AlCl3 processes, the 12 and 20 cS PAOs are prepared at 96° C. and 79° C., significantly higher than the 50° C. and 24° C. used to produce similar viscosities of PAOs using the SiO2—AlCl2 catalysts. Higher reaction temperatures are known to promote isomerizations of the starting 1-decene as well as the oligomeric products and thus produce a more branched material with lower VI.

The number and weight average molecular weights of PAOs from the supported AlCl2 catalysts are similar to PAOs from the homogeneous processes (FIGS. 8 and 9). The heterogeneous process using batch-produced SiO2—AlCl2 produces PAOs with slightly broader molecular weight distributions of the PAOs from homogeneous processes as shown in FIG. 10. Products of the heterogenous process which are produced from continuous processes should provide products with narrower molecular weight distribution.

It is claimed:

1. A process for the production of hydrocarbon lubricant basestock which comprises:

contacting C2 to C20 alpha-olefin feedstock, or mixtures thereof, under heterogeneous oligomerization conditions with a catalyst composition consisting essentially of halides of a single metal component anchored on an adsorbent inorganic oxide solid by an oxygen-metal bond, which catalyst composition is prepared by a method consisting essentially of contacting an adsorbent inorganic oxide support containing surface hydroxyl groups with organic metal halide, under conditions sufficient for said organic metal halide to react with at least a portion of said surface hydroxyl groups wherein said metal is aluminum, and said adsorbent inorganic oxide support is selected from the group consisting of silica, silica-alumina, clay, crystalline porous silicates, silicoaluminophosphates, titania, vanadia, and rare earth oxides, wherein said organic metal halide has the formula RMXY wherein R is alkyl or aryl, M is aluminum, X is halogen and Y is selected from the group consisting of halogen, alkyl, alkenyl, aryl, alkoxy, and amido moities, and said RMXY further being selected from the group consisting of EtAlCl2, Me2AlCl, Et2AlCl, Et2AlCl/EtAlCl2, and Et2AlOMe wherein said contacting of feedstock is carried out in the presence of a promoter selected from the group consisting of water and methanol, to provide a reaction mixture containing said hydrocarbon lubricant basestock;

and separating and recovering said hydrocarbon lubricant basestock.

2. The process of claim 1 wherein said inorganic oxide is silica.

3. The process of claim 1 wherein said surface hydroxyl groups are silanol.

4. The process of claim 1 wherein said inorganic oxide support is heated at temperatures ranging from 100° to 900° C., prior to said contacting of the support.

5. The process of claim 4 wherein said inorganic oxide support is heated at temperatures ranging from 300° to 600° C. for 1 to 8 hours, prior to said contacting.

6. The process of claim 1 wherein said inorganic oxide support is a porous crystalline silicate selected from the group consisting of MCM-22 and MCM-41.

7. The process of claim 3 wherein RMXY is EtAlCl2 and said adsorbent is silica.

8. The process of claim 1 wherein said oligomerization conditions comprise temperatures of −70° to 250°

C., and said lubricant basestock comprises $C_{30}$ to $C_{1300}$ hydrocarbons, has a branch ratio of less than 0.25, a weight average molecular weight between 280 and 60,000, number average molecular weight between 280 and 20,000, molecular weight distribution between 1.01 and 3.0, a pour point below $-20°$ C., and a viscosity index greater than 80.

9. The process of claim 8 wherein said oligomerization temperature is $-20°$ to $180°$ C., and the yield of $C_{20}+$ oligomer is at least 85 wt % for product having a viscosity of at least 4.0 cS at $100°$ C.

10. The process of claim 8 wherein said olefin feedstock is selected from the group consisting of propylene, 1-butene, 1-pentene, 1-hexene, 4-methyl-1-pentene, 1-heptene, 1-octene, 1-decene, 1-dodecene, and 1-tetradecene.

11. The process of claim 8 wherein said olefin feedstock consists essentially of 1-decene.

12. The process of claim 1 wherein said oligomerizing of alpha-olefin feedstock is carried out simultaneously with said contacting of the adsorbent inorganic oxide support with said organic metal halide.

13. The process of claim 1 wherein said adsorbent has a pore size of 20 to 400 angstroms and a particle size of 1 to 400 mesh.

14. The process of claim 1 wherein said adsorbent has a pore size of 40 to 400 angstroms and a particle size of 35 to 400 mesh.

15. The process of claim 1 wherein said lubricant basestock contains less than 100 ppm Cl.

* * * * *